United States Patent [19]

Sigg et al.

[11] Patent Number: 5,426,195
[45] Date of Patent: Jun. 20, 1995

[54] PROCESS FOR THE CATALYTIC DEHYDROGENATION OF DIOLS

[75] Inventors: Reinhard Sigg; Hans Regner, both of Marl, Germany

[73] Assignee: Huels Aktiengesellschaft, Marl, Germany

[21] Appl. No.: 243,794

[22] Filed: May 17, 1994

[30] Foreign Application Priority Data

Jun. 11, 1993 [DE] Germany ............... 43 19 456.7

[51] Int. Cl.$^6$ ........................................... C07D 307/02
[52] U.S. Cl. ..................................... 549/295; 549/266
[58] Field of Search ........................... 549/266, 295

[56] References Cited

U.S. PATENT DOCUMENTS

| | | | |
|---|---|---|---|
| 3,923,835 | 12/1975 | Smith | 549/326 |
| 4,070,375 | 1/1978 | Suzuki | 549/274 |
| 4,082,748 | 4/1978 | Shier | 544/98 |
| 4,091,041 | 5/1978 | Smith | 568/865 |
| 4,166,821 | 9/1979 | Suzuki | 549/274 |
| 4,384,146 | 5/1983 | Tang | 568/861 |
| 4,965,378 | 10/1990 | Budge et al. | 549/508 |
| 5,072,009 | 12/1991 | Budge et al. | 549/508 |
| 5,106,995 | 4/1992 | Plotkin | 549/295 |

FOREIGN PATENT DOCUMENTS

WO92/00973 1/1992 WIPO .

OTHER PUBLICATIONS

Industrial Brochure of Mallinckrodt Specialty Chemicals Company, "Catalyst Data Sheet," 3 pp. (date not available).
Industrial Brochure of Engelhard, "Harshaw Catalysts," pp. 25, 31, 46–47 (date not available).
Industrial Brochure of Sud–Chemie, "Katalysatoren Der Sud–Chemie A.G.," 2 pp. (date not available).
Tetrahedron Letters, vol. 22, No. 41, 1981, pp. 4073–4076, Bruno Berthon, et al., "Preparation D'Esters Par Deshydrogenation D'Alcools Primaires En Phase Liquide Catalysee Par L'Oxyde De Cuivre-Observations Preliminaires".
Data WPI, Derwent Publications, AN 86-329466/50, JP-A-61 246 173, Nov. 1, 1986.
Chemical Abstracts, vol. 106, No. 17, Apr. 27, 1987, AN 138244w, JP-A-61 246 173, Nov. 1, 1986.

*Primary Examiner*—C. Warren Ivy
*Assistant Examiner*—A. A. Owens
*Attorney, Agent, or Firm*—Oblon, Spivak, McClelland, Maier & Neustadt

[57] ABSTRACT

Diols of 3 to 10 carbon atoms are catalytically dehydrogenated over a catalyst containing copper and chromium in a first stage in which the diols are passed in the liquid phase over the catalyst, and subsequently the reaction product obtained is passed in the gas phase over the catalyst.

7 Claims, No Drawings

PROCESS FOR THE CATALYTIC DEHYDROGENATION OF DIOLS

BACKGROUND OF THE INVENTION

1. Field of the Invention

The invention relates to a process for the catalytic dehydrogenation of diols with 3 to 10 carbon atoms on a catalyst containing copper and chromium.

2. Discussion of the Background

When diols are catalytically dehydrogenated the product formed is mainly formed of aldehydes and lactones. These products are used, inter alia, as perfumes, are employed as solvents and, furthermore, find utility as precursors for pharmaceutical products and polymers.

The catalytic dehydrogenation of alcohols or diols on catalysts containing copper and chromium is generally known. The preparation of lactones by dehydrogenation over copper oxide in the liquid phase is described (see Be. Berthon et al., Tetrahedron Letters 22 (41) 4073-6 (1961)). The use of Cu/Cr catalysts with and without added BaO for the dehydrogenation of alcohols is moreover disclosed in industrial brochures, for example of Südchemie, Mallinckrodt and Harshaw (Engelhard).

JP-A 61/246173 discloses the preparation of γ-butyrolactone by the dehydrogenation of butanediol over Cu/Cr/Mn or Cu/Cr/Zn catalysts. Hydrogen is added to the reaction medium to increase the useful life of the catalyst. According to WO 92/00 973 (U.S. Pat. No. 5,110,954) diols are dehydrogenated in the liquid phase using a finely divided, suspended copper oxide or copper/chromium catalyst. The dehydrogenation can be carried out according to the prior art in the liquid phase over fixed bed catalysts or in suspension as well as in the gas phase over fixed bed catalysts.

The disadvantage of gas-phase dehydrogenation is the relatively fast inactivation of the catalyst. In addition, the selectivity to product is reduced at the relatively high reaction temperatures which are required. Attempts to increase the useful life of the catalyst by adding additional hydrogen by reducing the boiling points of the diols, which are usually high, by dilution with inert gas and thus to increase the selectivity, do indeed lead to slight improvements but, at the same time, adversely affect the economics of the process.

Liquid-phase dehydrogenation suffers from selectivities which are too low and conversions which are too small.

SUMMARY OF THE INVENTION

Accordingly, one object of the invention is to provide an economic process for the catalytic dehydrogenation of diols which is distinguished by high selectivity and high conversion.

Another object of the invention is to provide a dehydrogenation process in which the useful life of the dehydrogenation catalyst containing copper and chromium is prolonged.

Briefly, these objects and other objects of the invention as hereinafter will become more readily apparent, can be attained in a process of dehydrogenating diols by 3 to 10 carbon atoms over a Cr—Cu catalyst in two stages by conducting a first stage dehydrogenation of a diol(s) in the liquid phase over the catalyst, and subsequently conducting a second stage dehydrogenation of the product of the first stage in the gas phase over the catalyst.

DETAILED DESCRIPTION OF THE PREFERRED EMBODIMENTS

It has now been found, surprisingly, that a very high selectivity to product and virtually complete conversion of starting diol can be achieved when the catalytic dehydrogenation of a diol(s) is carried out in two stages by first passing the diol reactant in the liquid phase over a dehydrogenation catalyst and subsequently passing the reaction mixture obtained in the gas phase over the catalyst. It is very surprising that when the reaction is carried out in these two stages, the catalysts containing copper and chromium retain a long useful life although a gas-phase process takes place in the second stage where no additional hydrogen is supplied to the reaction.

The present invention thus is a two-stage process for the catalytic dehydrogenation of diols with 3 to 10 carbon atoms on a catalyst containing copper and chromium, in which, in the first stage the diols are passed in the liquid phase over the catalyst, and subsequently the reaction mixture obtained is passed in the gas phase over the catalyst.

The dehydrogenation is preferably carried out under atmospheric pressure or under slightly elevated pressure. Slightly the elevated pressures are appropriately no higher than 3 bar abs.

The dehydrogenation according to the invention is carried out in two stages. The initial stage is a liquid phase dehydrogenation, while the second stage occurs and is a "finishing dehydrogenation". The final residues of the starting material are converted in the "finishing dehydrogenation" in the gas phase in the 2nd stage. Thus, it is possible and desirable for the conversion of the diol in the liquid phase in the 1st stage to be about 70 to 95%, preferably about 90%. The dehydrogenation according to the invention takes place both in the liquid phase and in the gas phase on known catalysts containing copper and chromium as are described, together with their preparation processes, in the prior art cited above, such as, for example, in JP-A 86/246 173. It is also possible to employ all commercially available catalysts containing copper and chromium, such as, for example, copper chromite catalysts in granular form.

In JP 61-246173-A, the preparation of γ-butyrolactone is described by the dehydrogenation of 1,4-butanediol over a copper-chromium-manganese (or zinc) catalyst. Preferred catalyst embodiments include (1) Cu—Cr =30–60 parts by weight:70–40 parts by weight; (2) Mn:(Cu +Cr) =3–20 parts by weight:100 parts by weight; (3) Zn:(Cu +Cr) =20–50 parts by weight:100 parts by weight. Dehydrogenation of 1,4-butanediol to γ-butyrolactone is conducted at 150°–300° C., preferably 200°–250° C., under an atmospheric pressure of 0–10,preferably 0–5, kg/$^2$cmG at a WHSV of 0.1–10,preferably 0.5–3,per hour.

A copper-chromium-manganese catalyst is prepared by dissolving 126.1 g of ammonium dichromate in distilled water (500 ml) and to this solution 28% ammonia water (150 ml) is added. To this solution is added 241.6 g of Cu(NO$_3$)$_2$.3H$_2$O, 28.7 g of Mn(NO$_3$)$_2$ and 500 ml of distilled water. The precipitate obtained is filtered, washed, dried and pulverized. It is then sintered at 350° C. and finally molded with 3–5% carbon to prepare a catalyst. The ratio of the metal components in the catalyst is 55:45:5.3.

A 29 g amount of catalyst is packed into a stainless steel reactor, and then the reactor is heated to 205° C. 1,4-Butanediol is diluted with hydrogen, pre-heated to 200° C. and then fed into the reactor at a WHSV of 1.5/hr. The amount of 1,4-butanediol fed into the reactor is 43.0 g/hr. The composition of the dehydrated product is: γ-butyrolactone (97.8 wt. %) unreacted 1,4-butanediol (0.5 wt. %) and by-products (1.7 wt. %).

The dehydrogenation according to the invention should take place under mild temperature conditions both in the liquid and in the gas phase. The boiling points of the diols employed must be taken into account in the dehydrogenation temperature selected.

The reaction product removed in the liquid phase from the 1st stage is, after further heating, passed entirely into the second stage of the gas-phase dehydrogenation.

The dehydrogenation in the gas phase in the 2nd stage takes place without the presence of additional hydrogen.

The dehydrogenation process according to the invention is suitable for a wide variety of diols. It is also possible to dehydrogenate diols with one or more ether linkages in the molecule, such as, for example, diethylene glycol.

It is possible and preferred to dehydrogenate alkanediols by the process of the invention, and 1,4-butanediol can be preferably dehydrogenated.

The process according to the invention can be carried out in such a way that the dehydrogenation in the liquid phase takes place in a first reactor and the "finishing dehydrogenation" in the gas phase then takes place in a second reactor.

The dehydrogenation of 1,4-butanediol by the present process can be carried out under mild conditions at temperatures from 150° to 220° C. in the liquid phase and then at temperatures from 180° to 240° C. in the gas phase. Thus, in a preferred embodiment, 1,4-butanediol is passed over a catalyst as the first stage in the liquid phase at temperatures from 150° to 220° C. and subsequently the reaction product obtained is passed in the gas phase at temperatures from 180° to 240° C. over the catalyst.

Having generally described this invention, a further understanding can be obtained by reference to certain specific examples which are provided herein for purposes of illustration only and are not intended to be limiting unless otherwise specified.

EXAMPLE 1

1,4-Butanediol, which has been preheated to 190° C., is dehydrogenated in a first stage over a commercial Cu/Cr catalyst (Mallinckrodt E 406 Tu ⅛ inch) of 42% by weight Cu and 40% by weight Cr, which is stabilized with 8% by weight BaO, in a fixed bed reactor at a temperature of 200° C. The fixed bed reactor is heated with heat-transfer oil, and the heat input is such as to ensure that the endothermic reaction (120 kjoule/kmol) is carried out as an isothermal reaction. The 1,4-butanediol is passed through the catalyst bed from the bottom to the top at an LHSV of 0.3-5 $h^{-1}$. The butyrolactone/1,4-butanediol mixture is drawn off at the top of the reactor and further heated to about 220° C. and then passed in the form of a gas from the bottom to the top through a second catalyst bed, which is likewise heated with heat-transfer oil, at a temperature of 230° C. and at a WHSV of 0.3-5 $h^{-1}$.

The 1,4-butanediol conversion is greater than 99% with a γ-butyrolactone selectivity of 97.8%. By-products comprise small amounts of hydroxybutyraldehyde and cyclic acetal (tetrahydrofuran butanediol acetal).

EXAMPLE 2

The 1,4-butanediol dehydrogenation is carried out continuously for over 2000 h under the reaction conditions of Example 1. The conversion and the selectivity remain virtually constant at the values of Example 1 when the reaction temperatures remain the same at 190° to 205° C. in the first catalyst bed and 220° to 235° C. in the second catalyst bed.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A two-stage process for the dehydrogenation of diols with 3 to 10 carbon atoms on a catalyst containing copper and chromium in two stages, comprising:
    conducting a first stage dehydrogenation of a diol(s) in the liquid phase over the catalyst; and subsequently
    conducting a second stage dehydrogenation of the product of the first stage in the gas phase over the catalyst.

2. The process according to claim 1, wherein the dehydrogenation is carried out under atmospheric pressure or slightly elevated pressure.

3. The process according to claim 1, wherein the starting diol(s) contains one or more ether linkages in the molecule.

4. The process according to claim 1, wherein said diol starting material is alkanediols.

5. The process according to claim 4, wherein said alkanediol is 1,4-butanediol.

6. The process according to claim 5, wherein 1,4-butanediol is first passed in the liquid phase at temperatures from 150° to 220° C. over the catalyst, and subsequently the reaction product obtained is passed in the gas phase at temperatures from 180° to 240° C. over the catalyst.

7. The process according to claim 1, wherein the conversion of diol reactant in the liquid phase of the first stage ranges from 70 to 95%.

* * * * *